US012678633B2

(12) United States Patent
Farmer et al.

(10) Patent No.: US 12,678,633 B2
(45) Date of Patent: Jul. 14, 2026

(54) FORMULATION AND DEVICE FOR COSMETIC TREATMENT OF ONYCHOMYCOSIS

(71) Applicant: Scholl's Wellness Company LLC, Parsippany, NJ (US)

(72) Inventors: Edmund Farmer, Seymour, CT (US); Bruce Nelson, Lakeland, TN (US)

(73) Assignee: Scholl's Wellness Company LLC, Parsippany, NJ (US)

( * ) Notice: Subject to any disclaimer, the term of this patent is extended or adjusted under 35 U.S.C. 154(b) by 1209 days.

(21) Appl. No.: 17/581,999

(22) Filed: Jan. 24, 2022

(65) Prior Publication Data

US 2022/0249859 A1 Aug. 11, 2022

Related U.S. Application Data

(60) Provisional application No. 63/147,734, filed on Feb. 9, 2021.

(51) Int. Cl.
| | |
|---|---|
| *A61K 8/22* | (2006.01) |
| *A45D 37/00* | (2006.01) |
| *A61N 5/06* | (2006.01) |
| *A61Q 3/00* | (2006.01) |

(52) U.S. Cl.
CPC ............. *A61N 5/062* (2013.01); *A45D 37/00* (2013.01); *A61K 8/22* (2013.01); *A61Q 3/00* (2013.01); *A45D 2200/1036* (2013.01); *A45D 2200/25* (2013.01); *A61N 2005/0626* (2013.01); *A61N 2005/0645* (2013.01); *A61N 2005/0651* (2013.01); *A61N 2005/0663* (2013.01)

(58) Field of Classification Search
CPC ............ A61N 5/062; A61N 2005/0626; A61N 2005/0645; A61N 2005/0651; A61N 2005/0663; A61N 2005/0662; A61N 5/0624; A61N 5/0616; A45D 37/00; A45D 2200/1036; A45D 2200/25; A45D 29/00; A45D 2200/205; A61K 8/22; A61Q 3/00
See application file for complete search history.

(56) References Cited

U.S. PATENT DOCUMENTS

| | | | |
|---|---|---|---|
| 9,561,276 | B2 | 2/2017 | Lundahl |
| 2008/0058905 | A1 | 3/2008 | Wagner |
| 2009/0234270 | A1 | 9/2009 | Loebel et al. |
| 2010/0098645 | A1* | 4/2010 | Barrett ............... A61K 31/7004 424/94.4 |
| 2011/0200544 | A1* | 8/2011 | Chesnoy ................ A61K 31/17 424/61 |
| 2012/0283622 | A1 | 11/2012 | Nath |
| 2014/0275254 | A1* | 9/2014 | Karlsson ................ A61K 31/19 514/557 |
| 2016/0120803 | A1* | 5/2016 | Mathur ................ A61K 8/4993 514/169 |

FOREIGN PATENT DOCUMENTS

| | | |
|---|---|---|
| BR | PI08052948 | 8/2010 |
| EP | 2777689 | 9/2014 |
| WO | 2013005156 | 1/2013 |

OTHER PUBLICATIONS

"Nail Fungus", URL: http://www.mayoclinic.org/diseases-conditions/nail-fungus/symptoms-casuses/syc-20353294, retrieved on Mar. 17, 2022, 4 pages.
International Search Report and Written Opinion for PCT/US2022/013603 mailed May 24, 2022, 13 pages.
Supplementary European Search Report received for European Patent Application No. 22753119.1, dated Nov. 29, 2024, 7 pages.

* cited by examiner

*Primary Examiner* — Jessica Worsham
(74) *Attorney, Agent, or Firm* — Lowenstein Sandler LLP

(57) ABSTRACT

A method of treating a fungal infection of the nails is disclosed herein. In one embodiment, the treatment method comprises applying a formulation directly to a nail, wherein the formulation comprises bleaching and moisturizing agents to improve cosmetic appearance of the nail. In another embodiment, the treatment method comprises a formulation applied directly to a nail, wherein the formulation is subsequently exposed to a light source to improve efficacy of the formulation applied to the nail.

14 Claims, 2 Drawing Sheets

FORMULATION AND DEVICE FOR COSMETIC TREATMENT OF ONYCHOMYCOSIS

CROSS-REFERENCE TO RELATED APPLICATION(S)

This application claims the benefit of priority of U.S. Provisional Patent Application No. 63/147,734, filed on Feb. 9, 2021, the disclosure of which is hereby incorporated by reference herein in its entirety.

BACKGROUND

Fungal nail infection, known as onychomycosis, is a common condition that causes discoloration, thickening or separation of a nail.

With the exception of FDA approved oral medications or laser therapy, current solutions for treating onychomycosis are limited. Available over-the-counter (OTC) solutions are not curative, but rather are cosmetic and are aimed primarily at improving the appearance of fungal nails through hydration, debridement, and bleaching agents. Despite the availability of current OTC solutions directed at improving the cosmetic appearance of onychomycosis, their applications are often considered cumbersome, undesirable, or simply ineffective.

Accordingly, there is a need for an improved method to cosmetically treat onychomycosis.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

DETAILED DESCRIPTION

Figure 1A:
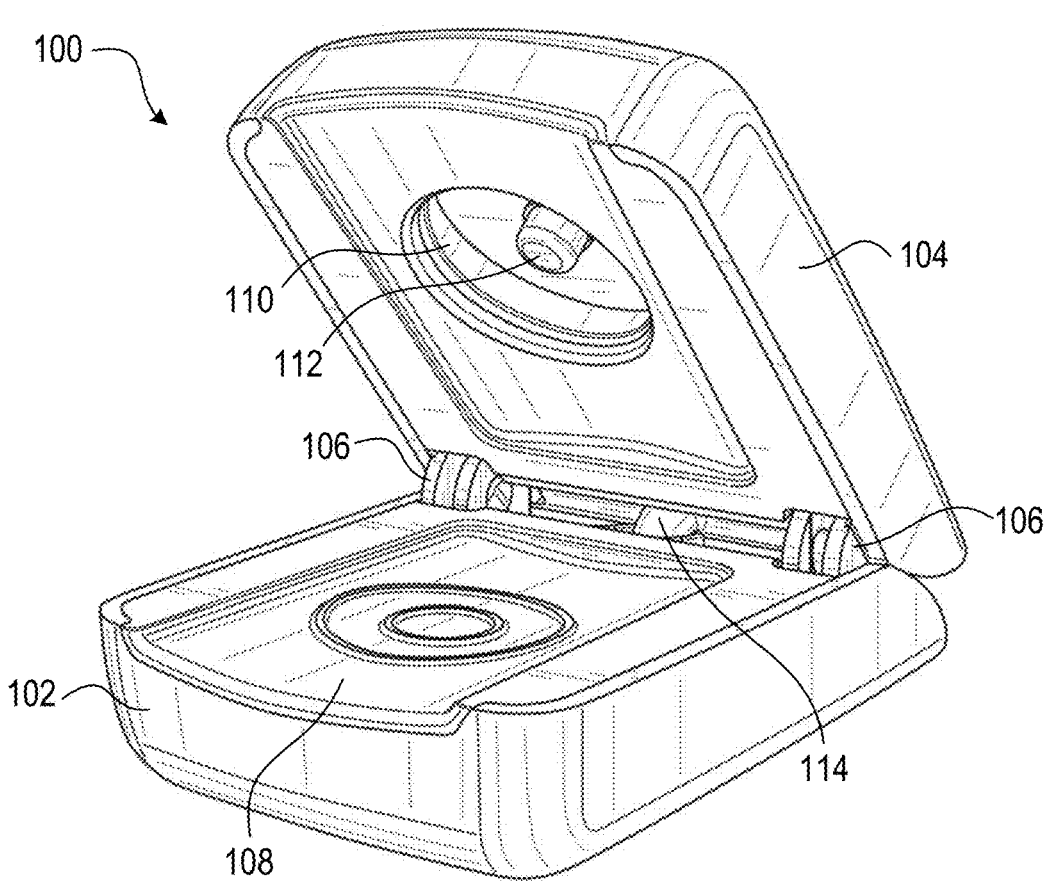
FIG. 1A illustrates an exemplary illumination device in an opened configuration in accordance with at least one embodiment.

A cosmetic treatment comprising a formulation that helps moisturize and lighten discolored nails is described herein, the efficacy of which may be improved when used in combination with an illumination device.

Certain embodiments of the illumination device described herein, when used in combination with a formulation comprising a photochemically active compound topically applied to a surface of a nail (e.g., of a human subject), provide for an improved reduction of nail discoloration from onychomycosis. More specifically, certain embodiments of the illumination device comprise an LED arrangement configured to emit light with a wavelength in the range of 400 nm to 500 nm, with any heat generation being undetectable or nearly undetectable by a human subject. The light emitted by the illumination device allows the activity of components of the formulation, such as bleaching agents, to be more effective in managing stains of discolored fungal nails, enabling a broader spectrum of stain treatment for discolored nails.

The formulations, devices, and methods of treatment described herein are exemplary embodiments and are not intended to be limiting in scope.

As used herein, the term "about" is used to describe and account for small fluctuations. For example, "about" may mean the numeric value may be modified by $\pm 1\%$, $\pm 0.5\%$, $\pm 0.4\%$, $\pm 0.3\%$, $\pm 0.2\%$, $\pm 0.1\%$, or $\pm 0.05\%$. All numeric values are modified by the term "about" whether or not explicitly indicated. Numeric values modified by the term "about" include the specific identified value. For example, "about 5.0" includes 5.0.

Unless otherwise indicated, all parts and percentages are by weight.

Exemplary Topical Formulations

Certain embodiments utilize formulations that include one or more photochemically active compounds. As used herein, the term "photochemically active compound" refers to a chemical compound for which exposure to light causes the chemical compound to undergo a chemical reaction or increases the chemical activity or efficiency of the chemical reaction.

Exemplary photochemically active compounds include peroxide-based bleaching agents. Peroxides will chemically react to form oxygen and water. In the transition from peroxide to oxygen and water, reactive intermediate products are formed, specifically, peroxide ions, peroxy radicals, and active oxygen, which are all referred to as active oxygen species. As reactive intermediates, these compounds have a very short lifetime. The use of visible light (e.g., non-ultraviolet light in a wavelength range of 400 nm to 500 nm) can accelerate the breakdown of the available concentration of peroxide, resulting in greater levels of available intermediates in a shorter period of time. The increased amount of intermediates available in turn results in increased bleaching activity and neutralization of colored compounds when applied to an affected nail.

In at least one embodiment, the formulation may be an aqueous composition comprising a plurality of components, such as one or more photochemically active compounds. For example, the one or more photochemically active compounds may comprise one or more bleaching agents. In at least one embodiment, the bleaching agent comprises one or more peroxides, such as urea peroxide, hydrogen peroxide, benzoyl peroxide, carbamide peroxide, or zinc peroxide.

In at least one embodiment, the formulation comprises one or more photochemically active compounds. The one or more photochemically active compounds may be present in an amount from about 5 wt. % to about 30 wt. %, from about 5 wt. % to about 10 wt. %, from about 10 wt. % to about 15 wt. %, from about 15 wt. % to about 20 wt. %, from about 20 wt. % to about 25 wt. %, or from about 25 wt. % to about 30 wt. %, calculated based on a total weight of the formulation. For example, in at least one embodiment, the formulation comprises one or more peroxides in an amount from about 15 wt. % to about 25 wt. %, calculated based on a total weight of the formulation.

In at least one embodiment, the formulation further comprises one or more carrier components, one or more hydration agents, one or more penetration modifiers, one or more buffering agents, one or more acidity regulators, one or more fixatives, one or more stabilizing agents, one or more skin conditioning agents, one or more humectants, one or more moisturizing agents, one or more emollients, one or more emulsifiers, one or more cleansing agents, one or more preservatives, or combinations thereof. In at least one embodiment, one or more components may provide two or more functions. For example, propylene glycol may function as both a carrier component and a hydration agent.

In at least one embodiment, the formulation comprises a carrier component (e.g., propylene glycol) from about 20 wt. % to about 80 wt. %, from about 30 wt. % to about 80 wt. %, from about 40 wt. % to about 80 wt. %, from about 50 wt. % to about 80 wt. %, from about 60 wt. % to about 80 wt. %, from about 70 wt. % to about 80 wt. %, from about 30 wt. % to about 70 wt. %, from about 30 wt. % to about 60 wt. %, from about 30 wt. % to about 50 wt. %, from about 30 wt. % to about 40 wt. %, from about 40 wt. % to about 60 wt. %, from about 40 wt. % to about 45 wt. %, from about 45 wt. % to about 50 wt. %, from about from about 50 wt. % to about 55 wt. %, or from about 55 wt. % to about 60 wt. %, calculated based on a total weight of the formulation.

In at least one embodiment, the formulation comprises water from about 5 wt. % to about 35 wt. %, from about 5 wt. % to about 10 wt. %, from about 10 wt. % to about 15 wt. %, from about 15 wt. % to about 20 wt. %, from about 20 wt. % to about 25 wt. %, from about 25 wt. % to about 30 wt. %, or from about 30 wt. % to about 35 wt. %, calculated based on a total weight of the formulation.

In an exemplary embodiment, the formulation comprises propylene glycol (e.g., from about 40 wt. % to about 60 wt. %), one or more peroxides (such as one or more of urea peroxide, hydrogen peroxide, benzoyl peroxide, carbamide peroxide, or zinc peroxide, e.g., from about 15 wt. % to about 25 wt. %), lactic acid (e.g., from about 1 wt. % to about 10 wt. %), triethyl citrate (e.g., from about 1 wt. % to about 5 wt. %), olive oil PEG-7 esters (e.g., from about 1 wt. % to about 5 wt. %), phenoxyethanol (e.g., from about 0.1 wt. % to about 1 wt. %), sodium hydroxide (e.g., from about 0.1 wt. % to about 1 wt. %), ethylhexylglycerin (e.g., from about 0.01 wt. % to about 1 wt. %), and water (e.g., from about 10 wt. % to about 30 wt. %). In at least one embodiment, the one or more peroxides comprises urea peroxide.

In a further exemplary embodiment, the formulation comprises propylene glycol, urea, glycerin, lactic acid, ozonated olive oil, sodium hydroxide, disodium EDTA, and water.

In a further exemplary embodiment, the formulation comprises calcium carbonate, Pef-8, urea, stearyl alcohol, mineral oil, glyceryl stearate, benzyl alcohol, cetyl alcohol, ceteareth-20, imidazolidinyl urea, dimethicone, and water.

In a further exemplary embodiment, the formulation comprises isopropanol, glycerine, citric acid, urea, d-panthenol, xanthan gum, sodium benzoate, pentaerythrityl tetra-di-t-butyl hydroxyhydrocinnamate, and water.

In a further exemplary embodiment, the formulation comprises ethyl lactate, glycerin, lactic acid, 4-acetyl resorcinol, citric acid, and water.

In a further exemplary embodiment, the formulation comprises propylene glycol, urea, glycerin, lactic acid, ozonated olive oil, sodium hydroxide, disodium EDTA, potassium perchlorate, and water.

In a further exemplary embodiment, the formulation comprises propylene glycol, urea, glycerin, lactic acid, ozonated olive oil, sodium hydroxide, disodium EDTA, sodium chlorate, and water.

In a further exemplary embodiment, the formulation comprises propylene glycol, urea, glycerin, lactic acid, ozonated olive oil, sodium hydroxide, disodium EDTA, sodium hypochlorite, and water.

In a further exemplary embodiment, the formulation comprises propylene glycol, urea, glycerin, lactic acid, ozonated olive oil, sodium hydroxide, disodium EDTA, one or more peroxides (comprising one or more of urea peroxide, hydrogen peroxide, benzoyl peroxide, carbamide peroxide, or zinc peroxide), and water.

In a further exemplary embodiment, the formulation comprises propylene glycol, urea, glycerin, lactic acid, melaleuca alternifolia (tea tree) leaf oil, sodium hydroxide, disodium EDTA and ozonated oil (comprising one or more of ozonated olive oil, ozonated linseed oil, ozonated avocado oil, ozonated coconut oil, ozonated lavender oil, ozonated jojoba oil, or ozonated safflower oil), and water.

Illumination Device

A photodynamic therapy device (hereinafter "illumination device") may be provided for use with the topical formulation comprising one or more photochemically active compounds. In one embodiment, the illumination device may be a small portable unit comprising a housing shaped and formed to allow for complete coverage of a nail. In another embodiment, the illumination device may be a stationary apparatus in a medical setting. Regardless of the form factor, an arrangement of one or more light emitting diodes (LEDs) may be housed in the body of the illumination device, which may be adapted with an illumination window, or other suitable opening, for directing light emitted by the LEDs onto the surface of the nail. The LED arrangement is configured to emit light with any heat generation being undetectable or nearly undetectable by a human subject. In at least one embodiment, the LED arrangement is configured to generate non-ultraviolet blue light in a wavelength range of 400-500 nm.

Figure 1B:
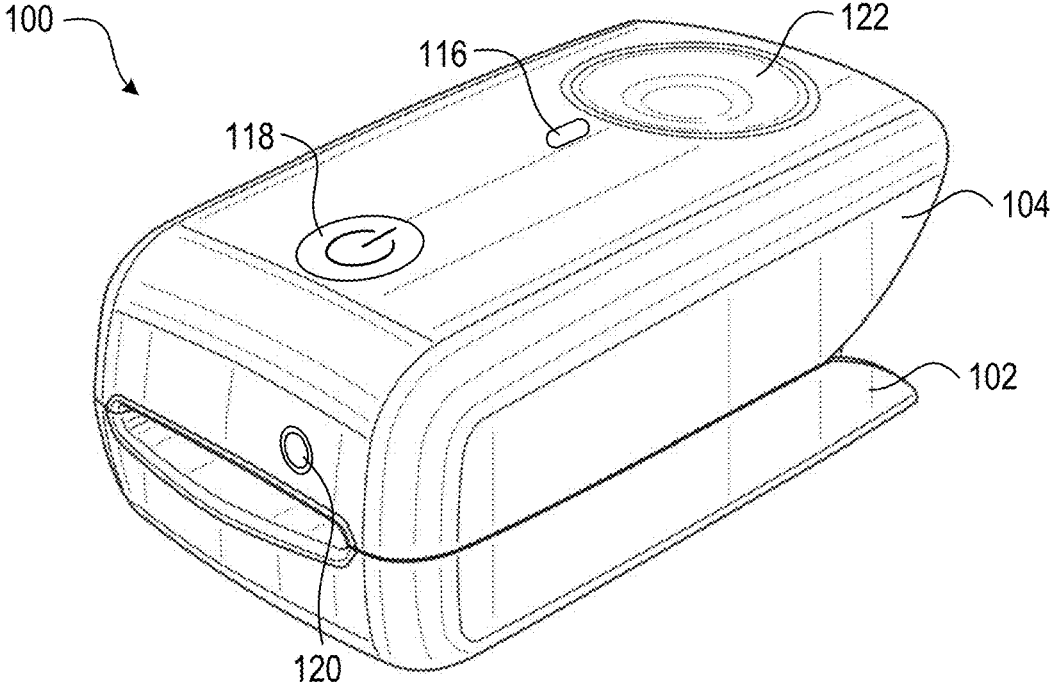
FIG. 1B illustrates the exemplary illumination device in a closed configuration in accordance with at least one embodiment.

FIGS. 1A and 1B illustrate an exemplary illumination device 100 in opened and closed configurations, respectively, in accordance with at least one embodiment. The illumination device 100, as illustrated, includes a base portion 102 and a lid portion 104 that collectively form a housing into which an individual can insert their finger or toe. The base portion 102 and the lid portion 104 are mechanically coupled via one or more hinges 106. In at least one embodiment, one or more of the hinges 106 includes a spring that is biased to maintain an open configuration or a closed configuration when no external mechanical forces are applied to the base portion 102 or the lid portion 104.

The base portion 102 includes a recessed bed portion 108 on which the individual can comfortably rest their finger or toe with the nail facing upward and away from the bed portion 108. A surface of the bed portion 108 may be textured to prevent slipping of the finger or toe and to facilitate comfort.

The lid portion 104 includes an aperture 110 inside which is housed an LED arrangement 112 comprising one or more LEDs configured for generating non-ultraviolet light, e.g., in a wavelength range of 400-500 nm (e.g., 400-410 nm, 410-420 nm, 420-430 nm, 430-440 nm, 440-450 nm, 450-460 nm, 460-470 nm, 470-480 nm, 480-490 nm, 490-500 nm, or within any arbitrary range defined between any of these endpoints). In at least one embodiment, aperture 110 may be shaped to correspond to the shape of a toenail or a fingernail, thereby increasing the surface area of the nail exposed to the light emitted by the LED arrangement.

In at least one embodiment, the lid portion 104 includes a button 118 that serves as a toggle power switch to electrically couple an on-board battery to the LED arrangement 112. In at least one embodiment, an indicator light 116 may be activated when the illumination device 100 is in an operational state (e.g., upon pressing the button 118). In at least one embodiment, the illumination device 100 may exit the operational state after reaching pre-determined time threshold (e.g., after about 1 minute, 5 minutes, etc.), after which the indicator light 116 turns off. In at least one embodiment, the on-board battery is a replaceable battery (e.g., an alkaline battery, a lithium ion battery, etc.), or a built-in battery that is rechargeable. For example, a port 120 (e.g., a Universal Serial Bus (USB) port, a Micro USB port, etc.) may be present on the illumination device 100 to which a power source may be connected for recharging the battery. In at least one embodiment, the device may be powered directly by an external power source without the use of an on-board battery. In at least one embodiment, a recessed region 122 is present on the lid portion 104 to allow the user to comfortably exert a force on the lid portion 104 to bias the illumination device 100 toward the closed configuration during use.

In at least one embodiment, an actuator 114 is present near the joint formed by the base portion 102 and the lid portion 104. The actuator 114 may be actuated only when the illumination device 100 is in the closed configuration, such that light is only emitted by the LED arrangement 112 upon closing the illumination device 100.

It is to be understood by those of ordinary skill in the art that the illumination device 100 depicted in FIGS. 1A and 1B is merely illustrative of a suitable device used in connection with the various methods described herein. Other variations may be utilized, including those for which one or more components are omitted or added. In at least one embodiment, an illumination device may include multiple units, for example, five units similar to the illumination device 100 that are mechanically coupled together or formed as a single unitary structure for which the individual can insert all five fingers or all five toes into different units simultaneously. In at least one embodiment, the base portion 102 and the lid portion 104 form a single unitary structure for which the hinges 106 are omitted and which may be shaped to receive and be securable to one or more of the individual's fingers or toes.

Method of Treatment

In at least one embodiment, a method of treatment comprises initially applying a formulation to a surface of an affected nail (e.g., a fungal nail), the formulation (as previously described) having a photochemically active compound to the nail. The formulation may be applied as a thin layer directly onto a surface of the nail using, for example, a brush, a cosmetic pen or any other suitable applicator. In at least one embodiment, the formulation may be sprayed onto the surface of the nail using a suitable spraying device. In at least one embodiment, the formulation may be incorporated into and/or coated onto a film strip adapted for an adhesive-like affixation to the surface of an affected nail, such that the film strip is infused with or adapted to release the formulation directly onto the surface of the affected nail.

After application of the formulation to an affected nail, an illumination device (e.g., the illumination device 100) may be positioned over or secured directly to the affected nail. Once the illumination device is properly placed, it may be activated to emit the desired treatment wavelength of light to the formulation applied to the affected nail to increase the efficacy of the formulation. A predetermined treatment time may be measured and, when satisfied, the illumination device may be powered off and, subsequently, removed from the affected nail.

Figure 2:
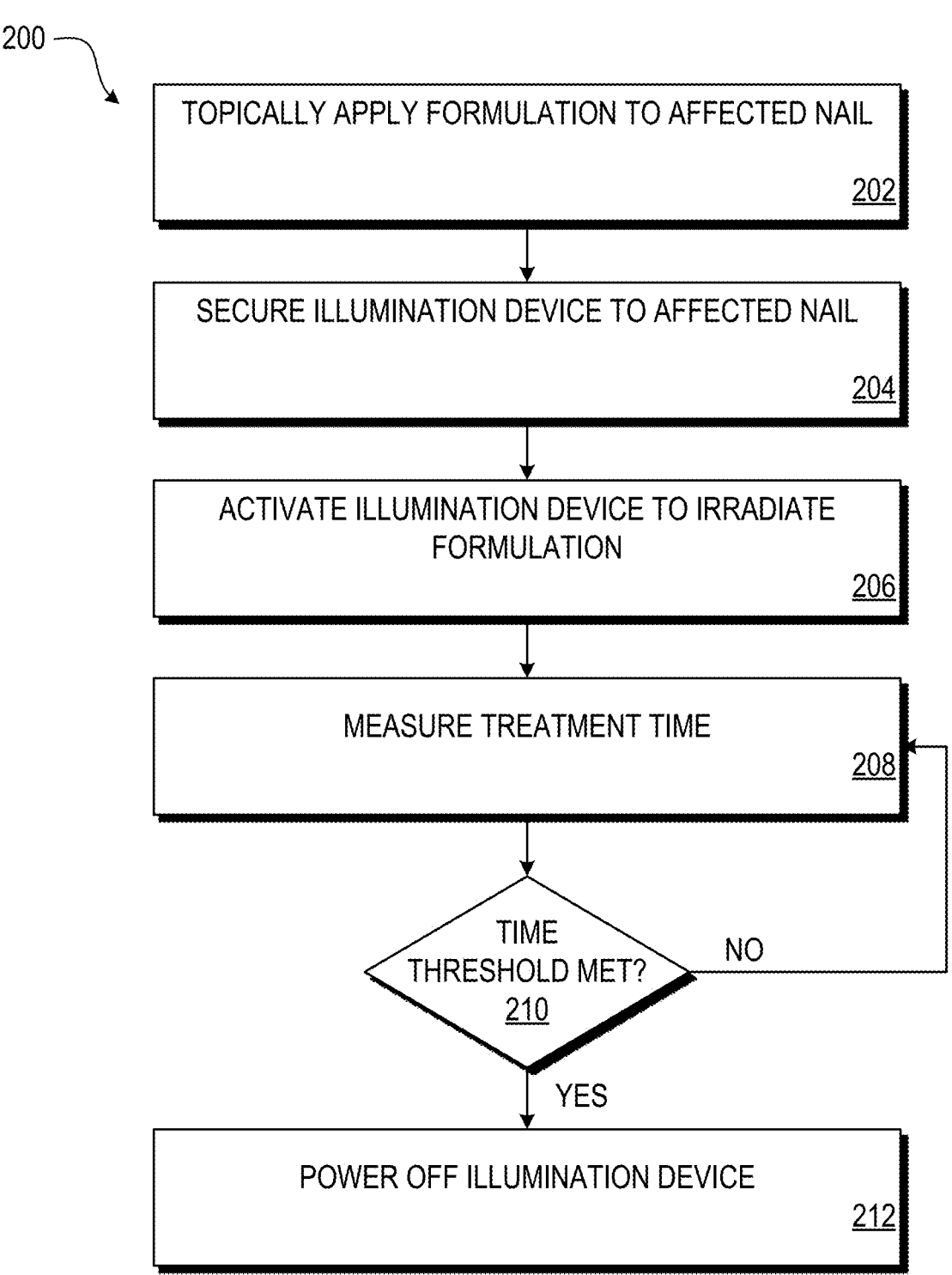
FIG. 2 is a flow diagram illustrating an exemplary method of cosmetically treating onychomycosis in accordance with at least one embodiment.

FIG. 2 is a flow diagram illustrating an exemplary method 200 of cosmetically treating onychomycosis in accordance with at least one embodiment. The method 200 begins at block 202, where a formulation is topically applied to an affected nail of an individual. The nail may be a fingernail or a toenail. In at least one embodiment, the formulation comprises a photochemically active compound. In at least one embodiment, the photochemically active compound is a bleaching agent. In at least one embodiment, the bleaching agent comprises one or more peroxides.

In at least one embodiment, the formulation is applied as a thin layer directly onto a surface of the nail. In at least one embodiment, the formulation is embodied in a film strip adapted to release the formulation when affixed onto a surface of the nail.

At block 204, an illumination device (e.g., the illumination device 100) is secured to the affected nail. For example the illumination device may be shaped to receive or be secured to a finger or toe of the affected nail. In at least one embodiment, the illumination device may be shaped to fit snugly against the finger or toe of the affected nail.

At block 206, the illumination device is activated to irradiate the formulation, for example, in response to actuating a button of the illumination device (e.g., actuating the button 118 and/or the actuator 114). In at least one embodiment, the illumination device comprises at least one light-emitting diode (LED) configured to emit non-ultraviolet light in a wavelength range of 400 nm to 500 nm (e.g., the LED arrangement 112). In at least one embodiment, irradiation of the formulation increases efficacy of the formulation applied to the fungal nail.

At block 208, the treatment time is measured, for example, by the individual or by a built-in timing circuit of the illumination device.

At block 210, if a time threshold condition is not met, then the method 200 proceeds to block 208 (e.g., in the embodiment for which a built-in timing circuit is utilized). Otherwise, the method 200 proceeds to block 212 where the illumination device is powered off. In at least one embodiment, the time threshold is about 30 seconds, 1 minute, 2 minutes, 3 minutes, 4 minutes, 5 minutes, 10 minutes, or longer.

The following summary of exemplary embodiments presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims.

Embodiment 1: a method of cosmetically treating onychomycosis, the method comprising: applying a formulation to a fungal nail, the formulation comprising a photochemically active compound; positioning an illumination device over the formulation applied to the fungal nail; and activating the illumination device to irradiate the formulation applied to the fungal nail.

Embodiment 2: the method of embodiment 1, wherein the illumination device comprises at least one light-emitting diode (LED) configured to emit non-ultraviolet light in a wavelength range of 400 nm to 500 nm.

Embodiment 3: the method of embodiment 1, wherein irradiation of the formulation increases efficacy of the formulation applied to the fungal nail.

Embodiment 4: the method of embodiment 1, wherein the illumination device is configured to power off automatically after a threshold treatment time is reached.

Embodiment 5: the method of embodiment 1, wherein the formulation is applied as a thin layer directly onto a surface of the nail.

Embodiment 6: the method of embodiment 1, wherein the formulation is embodied in a film strip adapted to release the formulation when affixed onto a surface of the nail.

Embodiment 7: the method of embodiment 1, wherein the photochemically active compound is a bleaching agent.

Embodiment 8: the method of embodiment 7, wherein the bleaching agent comprises one or more peroxides.

Embodiment 9: a treatment kit comprising: a revitalizer product suitable for application to a fungal nail; and an illumination device configured to emit light at a wavelength sufficient to improve efficacy of the revitalizer product when applied to the fungal nail.

Embodiment 10: the treatment kit of embodiment 9, wherein the illumination device is shaped to receive or be secured to the fungal nail.

Embodiment 11: the treatment kit of embodiment 9, wherein the revitalizer product comprises a formulation comprising at least one active ingredient for moisturizing the fungal nail.

Embodiment 12: the treatment kit of embodiment 9, wherein the revitalizer product comprises a formulation comprising at least one active ingredient for bleaching the fungal nail.

Embodiment 13: the treatment kit of embodiment 9, wherein the revitalizer product comprises a formulation comprising one or more peroxides present from about 15 wt. % to about 25 wt. %, calculated based on a total weight of the formulation.

Embodiment 14: the treatment kit of embodiment 13, wherein the one or more peroxides comprise urea peroxide.

Embodiment 15: the treatment kit of embodiment 14, wherein the formulation further comprises propylene glycol from about 40 wt. % to about 60 wt. %, calculated based on the total weight of the formulation.

Embodiment 16: the treatment kit of embodiment 15, wherein the formulation further comprises one or more of lactic acid, triethyl citrate, olive oil PEG-7 esters, phenoxyethanol, and ethylhexylglycerin.

Embodiment 17: the treatment kit of embodiment 9, wherein the illumination devices comprises an LED arrangement configured to emit a non-ultraviolet blue light in a wavelength range of 400-500 nm.

Embodiment 18: an illumination device comprising: an LED arrangement, the LED arrangement configured to emit a non-ultraviolet blue light in a wavelength range of 400-500 nm; and a mechanism for manipulating the device for secure attachment to a toenail or a fingernail.

Embodiment 19: the device of embodiment 18, further comprising a timing control component configured to measure treatment time, wherein the timing control component is further configured to automatically power off the LED arrangement upon determining a threshold treatment time is reached.

Embodiment 20: the device of embodiment 18, wherein the mechanism is operable as a spring loaded clamp adapted to accommodate an entire surface area of the toenail or the fingernail.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure. For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment" or "one embodiment" means that a particular feature, structure, or characteristic described in connection with the embodiment is included in at least one embodiment. Thus, the appearances of the phrase "an embodiment" or "one embodiment" in various places throughout this specification are not necessarily all referring to the same embodiment.

The present disclosure is not to be limited in scope by the specific embodiments described herein. Indeed, other various embodiments of and modifications to the present disclosure, in addition to those described herein, will be apparent to those of ordinary skill in the art from the description and accompanying drawings. Thus, such other embodiments and modifications are intended to fall within the scope of the present disclosure. Further, while the present disclosure has been described in the context of a particular embodiment in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein, along with the full scope of equivalents to which such claims are entitled.

The invention claimed is:

1. A method of cosmetically treating onychomycosis, the method comprising:

applying a formulation to a fungal nail, the formulation comprising urea peroxide from about 15 wt. % to about 25 wt. %, propylene glycol from about 40 wt. % to about 60 wt. %, triethyl citrate, lactic acid, and one or more olive oil PEG-7 esters, calculated based on a total weight of the formulation;

positioning an illumination device over the formulation applied to the fungal nail; and activating the illumination device to irradiate the formulation applied to the fungal nail.

2. The method of claim 1, wherein the illumination device comprises at least one light-emitting diode (LED) configured to emit non-ultraviolet light in a wavelength range of 400 nm to 500 nm.

3. The method of claim 1, wherein irradiation of the formulation increases efficacy of the formulation applied to the fungal nail.

4. The method of claim 1, wherein the illumination device is configured to power off automatically after a threshold treatment time is reached.

5. The method of claim 1, wherein the formulation is applied as a thin layer directly onto a surface of the nail.

6. The method of claim 1, wherein the formulation is embodied in a film strip adapted to release the formulation when affixed onto a surface of the nail.

7. The method of claim 1, wherein the urea peroxide functions as a bleaching agent.

8. A treatment kit comprising:

a revitalizer product suitable for application to a fungal nail, wherein the revitalizer product comprises a formulation comprising urea peroxide from about 15 wt. % to about 25 wt. %, propylene glycol from about 40 wt. % to about 60 wt. %, triethyl citrate, lactic acid, and one or more olive oil PEG-7 esters, calculated based on a total weight of the formulation; and an illumination device configured to emit light at a wavelength sufficient to improve efficacy of the revitalizer product when applied to the fungal nail.

9. The treatment kit of claim 8, wherein the illumination device is shaped to receive or be secured to the fungal nail.

10. The treatment kit of claim 8, wherein the revitalizer product comprises a formulation comprising at least one active ingredient for moisturizing the fungal nail.

11. The treatment kit of claim 8, wherein the urea peroxide functions as a bleaching agent for the fungal nail.

12. The treatment kit of claim 8, wherein the formulation further comprises phenoxyethanol.

13. The treatment kit of claim 12, wherein the formulation further comprises ethylhexylglycerin.

14. The treatment kit of claim 8, wherein the illumination device comprises an LED arrangement configured to emit a non-ultraviolet blue light in a wavelength range of 400-500 nm.

* * * * *